United States Patent

Mahmud-Durrani

Patent Number: 5,322,501
Date of Patent: Jun. 21, 1994

[54] CONTINENT URETHRAL STENT FOR TREATING AND PREVENTING URETHRAL STRICTURE AFTER SURGERY

[76] Inventor: Ayaz Mahmud-Durrani, 5003 Magnolia La., Bay City, Tex. 77414

[21] Appl. No.: 955,450
[22] Filed: Oct. 2, 1992
[51] Int. Cl.⁵ ............................................. A61M 5/00
[52] U.S. Cl. ......................................... 604/8; 604/54; 604/281; 606/108
[58] Field of Search ............... 604/8, 49, 54, 93, 104, 604/105, 280, 281; 606/108, 198

[56] References Cited

U.S. PATENT DOCUMENTS

| | | | |
|---|---|---|---|
| 2,649,092 | 8/1953 | Wallace | 604/105 |
| 3,915,171 | 10/1975 | Shermeta . | |
| 4,531,933 | 7/1985 | Norton et al. | 604/281 X |
| 4,610,657 | 9/1986 | Densow | 604/8 |
| 4,699,611 | 10/1987 | Bowden | 604/105 X |
| 4,738,667 | 4/1988 | Galloway | 604/54 X |
| 4,932,938 | 6/1990 | Goldberg et al. . | |
| 4,932,958 | 6/1990 | Reddy et al. . | |
| 4,973,301 | 11/1990 | Nissenkorn | 604/8 |
| 5,007,898 | 4/1991 | Rosenbluth et al. . | |
| 5,059,169 | 10/1991 | Zilber | 604/8 |
| 5,078,720 | 1/1992 | Burton et al. . | |
| 5,141,502 | 8/1992 | Macaluso, Jr. | 604/281 |
| 5,221,253 | 6/1993 | Coll | 604/8 |

Primary Examiner—John D. Yasko
Assistant Examiner—Frank Wilkens
Attorney, Agent, or Firm—Mason, Fenwick & Lawrence

[57] ABSTRACT

Disclosed is an apparatus and method for treating and preventing urethral stricture following surgery. The apparatus comprises a hollow cylindrical stent having a normally-expanded, contractible locating member attached at one end and a retrieving string attached at the other end. The contractible locating member is attached to the tube by two flexible strings. The contractible locating member is adjusted to its contracted condition by a cylindrical pusher prior to insertion into the bladder through the urethra. Once the contractible locating member is located in the bladder, the pusher is removed to permit the contractible locating member to return to its normally-expanded condition to provide an anchor in the bladder neck. The two strings connecting the stent and the contractible locating member are placed in the prostate and external sphincter, allowing the patient to remain continent. After healing is completed, the assembly can be retrieved by pulling the retrieving string.

20 Claims, 1 Drawing Sheet

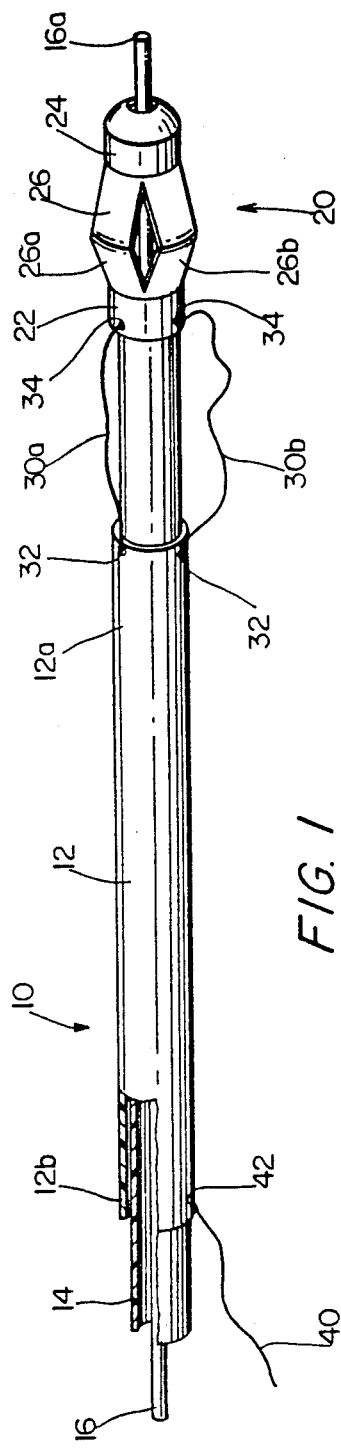
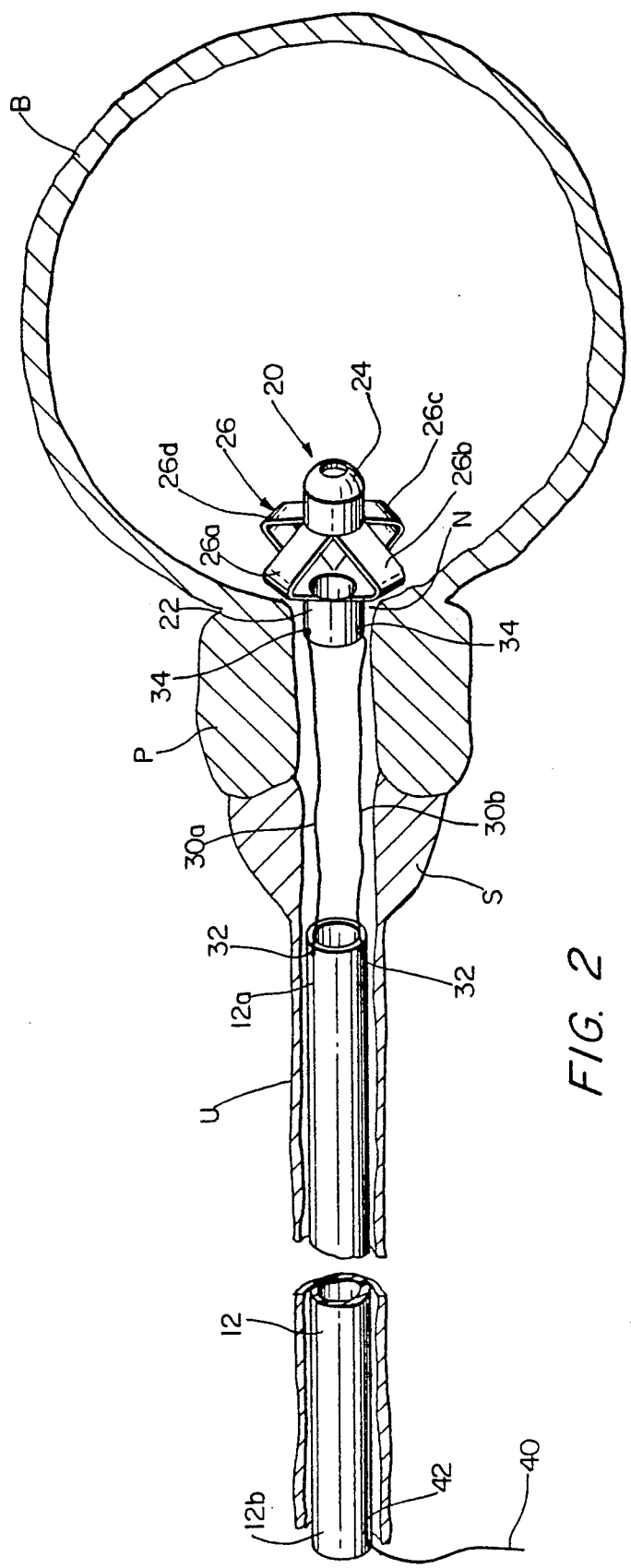

CONTINENT URETHRAL STENT FOR TREATING AND PREVENTING URETHRAL STRICTURE AFTER SURGERY

BACKGROUND OF THE INVENTION

1. Field of the Invention

The present invention relates to a urethral stent assembly. More specifically, the invention relates to a continent urethral stent assembly which can be used for treating and preventing urethral stricture following surgery, without the disadvantage of losing control on urination that all other types of catheter stents would have.

2. Related Art

The male urethra is a narrow membranous canal, extending from the neck of the bladder to the meatus urinarius at the end of the penis. The neck of the bladder is the point of commencement of the urethra. There is no tapering part, which would constitute a true neck. The bladder suddenly contracts to the opening of the urethra. The sphincters are located immediately below the neck of the bladder and around the commencement of the urethra. Their function is to shut off the bladder when the person is not urinating.

Urethral stricture is one of the oldest ailments reported to afflict man. Historically, the predominant cause was gonococcal urethritis, a disease presently enjoying a resurgence. With increased awareness of its danger, and with earlier and more appropriate treatment, the impact this disease has on the urethra has lessened in modern communities. The modern surgical era, particularly in recent years, has seen a significant change in the management of the disease.

After surgical correction of urethral stricture, followed by rejoining of the ends of the urethra, as well as after other similar surgical procedures affecting the urethra, there is a great natural tendency for the affected part of urethra to collapse and heal with scar tissue. Some patients will develop strictures again and require further surgery.

Urethral stents have long been used as a non-surgical alternative to the treatment of the symptoms of obstructive prostatism. U.S. Pat. No. 5,007,898 issued to Rosenbluth et al discloses an apparatus comprising an expandable dilatation catheter 18, a sheath 12, a dilatation balloon 62, a locating balloon 60, a flexible distal tip 14, a stylet 154, etc. The catheter is inserted into the urethra and remains within the irrigation conduit until the locating balloon is disposed within the bladder, at which time the stylet is removed. The locating balloon is inflated by an inflation conduit coupled to a source of pressurized fluid to force open the affected prostatic urethra and eliminate the obstruction.

Urethral stents have also been used to facilitate bladder drainage in individuals who are unable to initiate or control such drainage due to organic disability, immobility, or other physical impairment. U.S. Pat. No. 4,932,938 issued to Goldberg et al discloses a urethral indwelling catheter with incontinence control having a manually-manipulable control valve for controlling bladder drainage.

A stent placement instrument and method is disclosed by U.S. Pat. No. 5,078,720 to Burton et al. The Burton instrument comprises an elongated inner tube having an outer tube disposed along its axis adapted to carry and retain a self-expanding stent adjacent its proximal end, and an arrangement for releasing the stent, in combination with at least one of the following components: (a) a location member for positioning and fixing the instrument so that the stent is released at a desired location in the body canal, and (b) a member for releasing the stent in a retrograde manner. A method for placing a self-expanding stent in a body canal is also disclosed.

Other stents developed for use in urethra include the Urolume Wallstent developed by Medinvent and supplied by American Medical System, and an intra-prostate stent sold by Advance Surgical Intervention. However, these stents are made of metal wire mesh. They are left in the urethra permanently and therefore are subject to inherent complications resulting from leaving a foreign object in the body.

Structurally related to urethral stents is a gastrostomy tube disclosed by U.S. Pat. No. 3,915,171 to Shermeta. The gastrostomy tube is intended for insertion into the stomach to supply and remove fluid. The device comprises a conduit 45, first retention bulb 25, 35, second retention bulb 40, first closure means 20 and second closure means 47. The two bulbs structurally embrace the two walls to prevent leakage from the stomach and from and into the abdominal cavity. The device is preferably made entirely from medical grade silicone rubber.

The insertion and operation of the prior art stents are very cumbersome. Special instruments are required to insert and remove the stents. Additional apparatus has to be attached to inflate the balloon commonly used to retain prior art stents in place in the bladder. Users of the prior art stents cannot have normal control over urination. Thus, there is a need for a simple method and apparatus to effectively treat and prevent urethral stricture without the loss of normal control over urination.

SUMMARY OF THE INVENTION

It is therefore a primary object of the present invention to provide an effective method and apparatus to treat and prevent urethral stricture following surgery, without the loss of normal continent control over urination.

It is a further provide a urethral stent which prevents urethral stricture and which does not cause incontinence, so that users do not need to carry the urine collection bags.

It is another object to provide a simple device for preventing urethral structure which can be inserted and removed easily from the urethra with less patient discomfort.

These and other objects are achieved, according to the invention by a urethral stent assembly which comprises a hollow cylindrical tube having a normally-expanded, contractible locating member attached to its inner end by flexible strings and a flexible retrieving string connected to its outer end.

The urethral stent of the present invention has a locating member made of resilient and very flexible material, and thus has a normally expanded configuration. It is selectively adjustable to a contracted condition by a cylindrical pusher which is axially slidable within the cylindrical tube and is engageable with the leading end of the locating member. Once the contractible locating member is properly positioned in the bladder, the pusher is removed so that the contractible locating member expands automatically and provides an anchor at the bladder neck.

User continence with the present invention is achieved through the provision of the two strings connecting the contractible locating member and the inner end of the tube. The urethral stent is positioned in the urethra such that only the strings are present in the external sphincter and prostate. Therefore incontinence caused by stretching of the external urethral sphincter muscle can be avoided.

Easy retrieval of the stent from the urethra after the urethra is completely healed is accomplished by pulling the flexible retrieving string connected to the outer end of the stent.

BRIEF DESCRIPTION OF THE DRAWINGS

The invention is better understood by reading the following Detailed Description of the Preferred Embodiments with reference to the accompanying drawing figures, in which like reference numerals refer to like elements throughout, and in which:

FIG. 1 is a perspective view, with parts broken away, of a urethral stent assembly in accordance with the present invention, having a guide wire and a pusher inserted therein;

FIG. 2 is a cross-sectional view of a male urethra and bladder with the urethral stent of the present invention shown in perspective view operatively inserted therein.

DETAILED DESCRIPTION OF THE PREFERRED EMBODIMENTS

In describing preferred embodiments of the present invention illustrated in the drawings, specific terminology is employed for the sake of clarity. However, the invention is not intended to be limited to the specific terminology so selected, and it is to be understood that each specific element includes all technical equivalents which operate in a similar manner to accomplish a similar purpose.

As best seen in FIG. 1, the urethral stent assembly 10 of the present invention comprises a hollow cylindrical stent 12 having an inner end 12a and an outer end 12b. Stent 12 preferably is made of a plastic material which is nonirritating to urethral tissue, such as the plastic material sold under the trademark SCILASTIC.

An elongated cylindrical pusher 14 having an outer diameter slightly smaller than the inner diameter of stent 12 is axially slidable within stent 12. An axially elongated flexible guide wire 16 having a tapered guiding end 16a is disposed within pusher 14 collinear with the axis of the pusher 14. Guide wire 16 is axially movable with respect to the pusher 14 and stent 12 and can be either a wire spring or a solid wire with an outer plastic sheath.

Situated near the inner end 12a of the stent 12 is a normally-expanded, contractible locating member 20 formed of non-irritating plastic, which comprises a trailing tip 22, a leading tip 24, and a contractible portion 26 connecting trailing and leading tips 22 and 24. As can be seen from FIGS. 1 and 2, the distal end of leading tip 24 is rounded, to permit easy insertion in and passage through the urethra U.

The contractible portion 26 comprises multiple ribbons 26a, 26b, 26c, and 26d having a generally V-shaped longitudinal cross-section. They can be joined at their leading and trailing ends but are separated from each other between their leading and trailing ends so as to assume a normally-expanded position in which ribbons 26a, 26b, 26c, and 26d are spaced apart from each other to define a path of fluid flow therebetween, to allow fluid drainage from the bladder to the urethra. The guiding end 16a of the guide wire 16 extends through the contractible locating member 20.

Ribbons 26a, 26b, 26c, and 26d are made of a resilient and flexible material such that contractible locating member 20 is in its normally-expanded configuration, i.e. the configuration shown in FIG. 2 in which its circumference is greatest. Due to the flexible nature of contractible locating member 20, the exertion of force against the leading tip 24 by pusher 14 while the trailing tip 22 is held in place causes contractible locating member 20 to assume its contracted configuration, i.e. the configuration in which its circumference is reduced, as shown in FIG. 1. Once the pusher 14 is removed, the resilient nature of the contractible locating member 20 causes it to resume its normally-expanded configuration, as shown in FIG. 2.

Two flexible strings 30a and 30b connect the inner end 12a of the stent 12 with the trailing end 22 of the contractible locating member 20; and are attached to stent 12 and locating member 20 by means of holes 32 through the inner end 12a of stent 12 and holes 34 through the trailing end 22 of locating member 20. Strings 30a and 30b have a length sufficient to permit them to extend through the prostate and the external sphincter, and preferably are made of nylon or a similar, non-irritating material.

A retrieving string 40 is attached at the outer end of the stent 12, through hole 42, and is similarly made of nylon or another non-irritating material.

Prior to insertion of the stent assembly into the urethra, the guide wire 16 is passed into and along the urethra U into the bladder B in accordance with known procedures. The guide wire 16 provides an initial path through which the contractible locating member 20 and the stent 12 are guided. Once the guide wire 16 is in place, the contractible locating member 20 is adjusted to assume its contracted configuration by pushing the pusher 14 forwardly against the leading tip 24. The assembly can then be inserted via the external opening of the urethra U, the leading tip 24 of the contractible locating member 20 being passed into and along the urethra U into the bladder B. The assembly is inserted through the urethra U until the contractible locating member 20 is located inside the bladder B. The two strings 30a and 30b are positioned to extend through the prostate P and external sphincter S, with the stent 12 being positioned in the urethra U at a predetermined position outwardly of the prostate P and external sphincter S. The retrieving string 40 remains outside the body.

Once the assembly is properly positioned, the pusher 14 and the guide wire 16 are removed from the stent 12. The resilient ribbons 26a, 26b, 26c, and 26d of the contractible locating member 20 expand to a predetermined diameter so as to bear against the bladder neck N and resist pull-out of the stent 12 from the urethra U, as shown in FIG. 2. Once healing is complete, the stent 12 can be removed from the urethra U by pulling the retrieving string 40. Due to its flexibility, the contractible locating member 20 is caused to contract by the tension from the stent 12 and the strings 30a and 30b.

Modifications and variations of the above-described embodiments of the present invention are possible, as appreciated by those skilled in the art in light of the above teachings. For example, the number of the ribbons of the contractible locating member can be increased or decreased as long as they are spaced apart between their ends so that urine can drain to the urethra through the bladder neck. Also, the number of connecting strings connecting the contractible locating member to the stent can be increased. The size of the stent can vary to accommodate the different sizes of urethra in adults and also different sizes in pediatric patients.

It is therefore to be understood that, within the scope of the appended claims and their equivalents, the invention may be practiced otherwise than as specifically described.

What is claimed is:

1. A urethral stent assembly for insertion in a male urethra and bladder, comprising:
    a stent comprising a hollow cylindrical tube having an inner end and an outer end;
    locating means for placement in the bladder for fixing the position of said tube in the urethra, said locating means having a normally expanded condition and being selectively adjustable to a contracted condition; and
    flexible connecting means for placement in the prostatic urethra and connecting said inner end of said tube to said locating means, said flexible connecting means being separate from said hollow cylindrical tube.

2. The urethral stent assembly of claim 1, further comprising adjustment means for adjusting said locating means to said contracted condition.

3. The urethral stent assembly of claim 1, wherein said locating means comprises a leading tip, a trailing tip, and a normally-expanded, contractible connecting portion connecting said leading tip and said trailing tip, said connecting portion having a fluid flow path therethrough.

4. The urethral stent assembly of claim 3, wherein said connecting portion comprises multiple ribbons separated from each other along at least a portion of their length, said ribbons being formed of a flexible and resilient material.

5. The urethral stent assembly of claim 3, further comprising adjustment means for contracting said contractible connecting portion.

6. The urethral stent assembly of claim 5, wherein said adjustment means comprises a cylindrical body axially slidable within said cylindrical tube and engageable with said leading tip of said locating means.

7. The urethral stent assembly of claim 1, wherein said assembly further comprises guiding means for guiding said tube into the urethra and said locating means into the bladder.

8. The urethral stent assembly of claim 7, wherein said guiding means comprises an axially elongated guide wire.

9. The urethral stent assembly of claim 1, wherein said assembly further comprises retrieving means for retrieving said tube, said locating means, and said connecting means from the bladder and urethra.

10. The urethral stent assembly of claim 9, wherein said retrieving means comprises a flexible string attached to said tube.

11. The urethral stent assembly for insertion in a male urethra and bladder, comprising:
    a stent comprising a hollow cylindrical tube having an inner end and an outer end;
    locating means for placement in the bladder for fixing the position of said tube in the urethra, said locating means having a normally expanded condition and being selectively adjustable to a contracted condition; and
    flexible connecting means for placement in the prostatic urethra and connecting said inner end of said tube to said locating means, said flexible connecting means being separate from said hollow cylindrical tube;
    wherein said flexible connecting means comprises string means of sufficient length for permitting the inner end of said hollow cylindrical tube to be positioned in the urethra outwardly of the external sphincter while said locating means remains in its expanded condition inside the bladder.

12. The urethral stent assembly of claim 11, further comprising adjustment means for adjusting said locating means to said contracted condition.

13. The urethral stent assembly of claim 11, wherein said locating means comprises a leading tip, a trailing tip, and a normally-expanded, contractible connecting portion connecting said leading tip and said trailing tip, said connecting portion having a fluid flow path therethrough.

14. The urethral stent assembly of claim 13, wherein said connecting portion comprises multiple ribbons separated from each other along at least a portion of their length, said ribbons being formed of a flexible and resilient material.

15. The urethral stent assembly of claim 13, further comprising adjustment means for contracting said contractible connecting portion.

16. The urethral stent assembly of claim 15, wherein said adjustment means comprises a cylindrical body axially slidable within said cylindrical tube and engageable with said leading tip of said locating means.

17. The urethral stent assembly of claim 11, wherein said assembly further comprises guiding means for guiding said tube into the urethra and said locating means into the bladder.

18. The urethral stent assembly of claim 17, wherein said guiding means comprises an axially elongated guide wire.

19. A method for treating conditions of the male urethra, comprising the steps of:
    a) providing a stent comprising a hollow cylindrical tube having an inner end and an outer end;
    b) providing normally-expanded, but contractible locating means for fixing the position of said tube in the urethra;
    c) providing flexible connecting means for connecting said inner end of said tube to said locating means;
    d) providing a guide wire means for insertion into the urethra and for use in inserting said tube and said locating means into the urethra;
    e) adjusting the locating means to its contracted condition;
    f) inserting the locating means in the bladder and the stent into the urethra while the locating means is in its contracted condition, with the connecting means being positioned in the prostatic urethra; and
    g) allowing the locating means to resume its normally expanded condition after it has been located in the bladder.

20. The method of claim 19, including the additional step of:
    (h) extracting the stent to cause the locating means to assume its contracted position and then move outwardly along the urethra until it clears the outer end of the urethra.

* * * * *